United States Patent [19]

Tritsch

[11] 4,049,001
[45] Sept. 20, 1977

[54] DIAPER WITH RESEALABLE TAPE CLOSURE

[75] Inventor: Ludwig Tritsch, Wilmette, Ill.

[73] Assignee: Johnson & Johnson, New Brunswick, N.J.

[21] Appl. No.: 661,920

[22] Filed: Feb. 27, 1976

[51] Int. Cl.² .............................................. A61F 13/16
[52] U.S. Cl. .................................... 128/287; 128/284; 24/DIG. 11
[58] Field of Search ....................... 128/287, 289, 290; 24/67 AR, DIG. 11

[56] References Cited

U.S. PATENT DOCUMENTS

| | | | |
|---|---|---|---|
| 3,848,594 | 11/1974 | Buell | 128/284 |
| 3,930,503 | 1/1976 | Tritsch | 128/287 |
| 3,951,149 | 4/1976 | Ness et al. | 128/287 |
| 3,955,576 | 5/1976 | Safford | 128/287 |
| 3,967,622 | 7/1976 | Ceperitis | 128/287 |

Primary Examiner—Stephen C. Pellegrino

[57] ABSTRACT

A disposable diaper has an improved tape tab fastening means in which a first securing tape ribbon has a free end and a fixed end which is attached to the diaper. A second securing tape ribbon has a free working end, and a fixed end which is adhesively but releasably attached to the free end of the first securing tape ribbon. One face of the second securing tape ribbon is provided with an adhesive coating. The free end of the first securing tape ribbon is adapted to secure the diaper about an infant by adhesive attachment via the adhesive-coated face of the second securing tape ribbon. The free end of the first securing tape ribbon is separable from the fixed end of the second securing tape ribbon to permit the opening of an applied diaper for inspection, and to make the adhesive coating on the free end of the first securing tape ribbon available for use in refastening the diaper about the infant.

2 Claims, 7 Drawing Figures

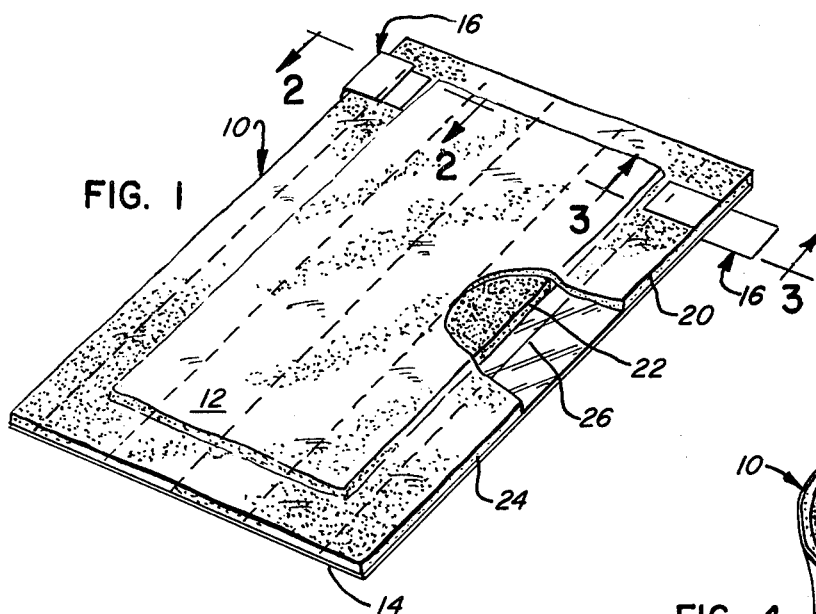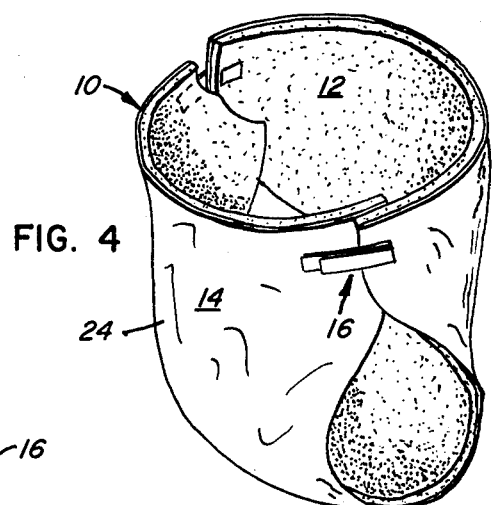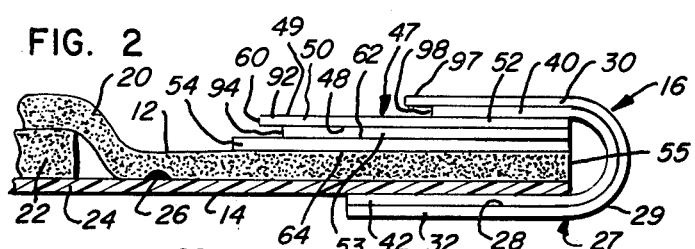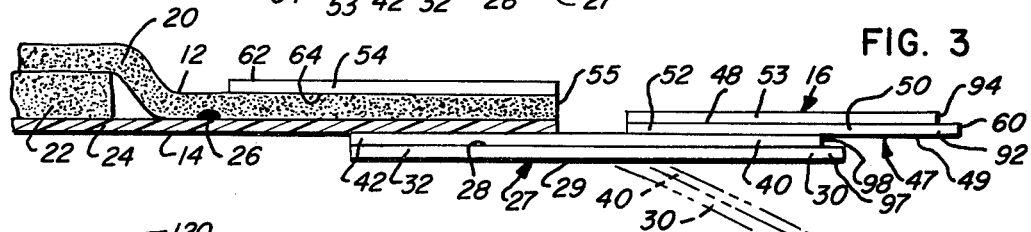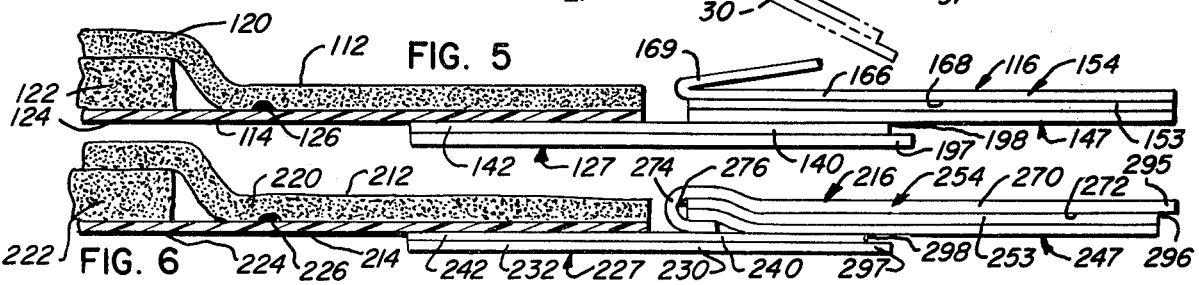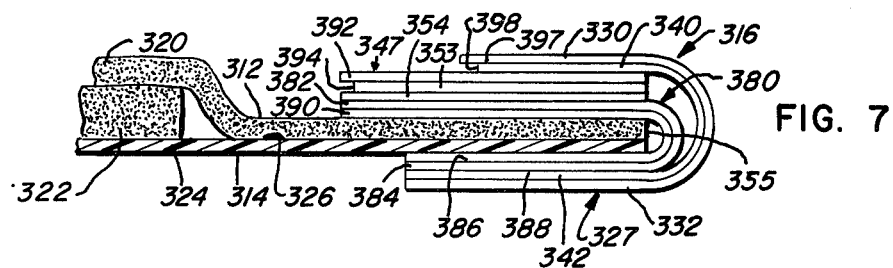

DIAPER WITH RESEALABLE TAPE CLOSURE

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions which eliminate the need for pins, for example, which present problems especially when the infant is active during the diaper changing.

Although tape tab fastening means have become a suitable substitute for extraneous fasteners such as pins, a suitable tape tab fastening system has not been developed to simulate the ability of an extraneous fastener to be opened and subsequently closed. For example, when using pin fastening, if a diaper needs checking to see if the diaper has been soiled, the pin permits opening, and if no soiling is evident, the diaper is again closed about the infant by repinning. Most prior tape tab systems have not provided this flexibility. The commercially available tape tabs which are used on disposable diapers cannot be disengaged readily to check for soiling or for repositioning the diaper. On most, if not all, occasions undesirable rupture of the outside sheet of the diaper occurs, or the tape tab itself is torn in checking the diaper. This tearing has made refastening unmanageable or impossible and frequently results in the loss of a possibly unsoiled diaper.

In an attempt to solve the foregoing problems, U.S. Pat. No. 3,848,596 to Pennau teaches a tape tab fastening means which allows an originally fastened diaper to be opened and subsequently closed. The tape tab consists of two adhesive areas on each tab covered by two release sheets. On the first closure, only one release sheet is removed to expose pressure-sensitive adhesive. Upon adjustment or inspection, the tape is peeled from the fastened position, or the tab torn, and the other release sheet is removed, exposing fresh adhesive for a subsequent fastening. This arrangement is practical for only two fastenings, the original and one more and has the serious drawback that undesirable rupture of the diaper can occur when peeling off the tape tab if the diaper user does not choose to tear the tab itself. With a torn fastening area, refastening is very difficult even with a freshly exposed adhesive area on the tape.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two interconnected tape portions which cause the folded configuration of the sealing tape to be somewhat bulky.

One of the embodiments disclosed in U.S. Pat. No. 2,932,747 to Dexter is a fastener having two overlapping gummed strips adhesively bonded together. The overlapping strip is attached to one fabric and the underlying strip is attached to another fabric. The adhesive bond between the two strips is the weakest link in the chain of attachment so that when the fastener is placed under stress, failure will occur between the two gummed strips before damaging loads can develop in the fabric. The adhesive on the overlapping strip terminates short of one end thereof to provide an unattached portion of the overlapping strips which can be grasped and peeled away from the underlying strip to sever the fabric joint.

Summary of the Invention

According to the present invenion, an improved economical tape tab system for use in disposable diapers permits an originally fastened diaper to be opened and reclosed several times without tearing the tape tab and without rupturing the diaper. Thus, the diaper can be opened and closed for inspection or adjustment many times during the normal service of the diaper. The original closure and the subsequent closings around the infant provide a good, strong adhesive attachment of the diaper.

The disposable diaper has a facing sheet defining a diaper inside surface, a backing sheet defining a diaper outside surface and an absorbent layer positioned therebetween. A first securing tape ribbon has a fixed end secured to the diaper, and a free working end. The first securing tape ribbon has an inner face which faces in the same direction as the diaper inside surface when the first securing tape ribbon is in an extended position.

A second securing tape ribbon has a free working end, and a fixed end which is adhesively but releasably attached to the inner face of the free working end of the first securing tape ribbon. The second securing tape ribbon has an outer face, and an inner face which is provided with a pressure-sensitive adhesive coating. The adhesive bond between the free working end of the first securing tape ribbon and the fixed end of the second securing tape ribbon is at least as strong as the bond between the fixed end of the first securing tape ribbon and the diaper outside surface.

Release means is provided for engagement with the adhesive-coated face of the second securing tape ribbon. In this manner, the second securing tape ribbon is separable from the release means to make the adhesive coating on the second securing tape ribbon available for use in securing the diaper about an infant.

The free working end of the first securing tape ribbon is separable from the fixed end of the second securing tape ribbon. The diaper can thereby be opened for inspection or adjustment, or removed from the infant. Once the free working end of the first securing tape ribbon is removed from the fixed end of the second, the adhesive coating on the free working end is exposed and available for use in refastening the diaper about the infant.

The improved tape tab system of the present invention will allow someone inspecting or adjusting the diaper to do so many times during the service of the diaper. Whereas many disposable diapers had to be discarded even when unsoiled because of torn tabs or rupture of the diaper, the improved system of the present invention provides the economical advantage of many inspections and repositionings of the diaper until soiled. Upon refastening, the tape tabs provide a good, strong securement to the diaper. Further features are the economy of manufacture, and, in some embodiments, a built-in release means which obviates the need for a removable cover strip.

Brief Description of the Drawing

FIG. 1 is a perspective view, partially broken away to show interior detail, of an open unfolded diaper in accordance with the present invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3, and showing in phantom the position which can be assumed by the detachable portion of the tab fastener of the present invention;

FIG. 4 is a perspective view of the diaper of FIG. 1 in a configuration assumed by the diaper when placed about an infant;

FIG. 5 is a fragmentary cross-sectional view similar to FIG. 3 and showing another embodiment of the invention;

FIG. 6 is a fragmentary cross-sectional view similar to FIGS. 3 and 5 and showing another embodiment of the invention; and FIG. 7 is a fragmentary cross-sectional view similar to FIGS. 3, 5 and 6 and showing another embodiment of the invention.

Description of the Preferred Embodiments

In the following description, two digit numerals are used to refer to the embodiment illustrated in FIGS. 1–4, three digit numerals in the one hundred series are used to refer to the embodiment illustrated in FIG. 5, three digit numerals in the two hundred series are used to refer to the embodiment illustrated in FIG. 6, and three digit numerals in the three hundred series are used to refer to the embodiment illustrated in FIG. 7. The same last two digits in each numeral designate similar elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tabs 16 are attached to diaper 10 for securing diaper 10 about an infant. As described in greater detail below, tabs 16 are movable from a folded-over storage position illustrated in FIG. 2 to a working position which is illustrated in FIG. 3.

Referring to FIGS. 1–3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots, or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 includes a first securing tape ribbon 27 having an inner face 28 and a outer face 29. First securing tape ribbon 27 has free working end 30 and a fixed end 32 which is permanently attached to a marginal portion of diaper 10, preferably along outer surface 14.

Adhesive coatings are provided on one face of free working end 30 and on a least one face of fixed end 32. An adhesive coating on both faces of fixed end 32 is desirable when the fixed end is sandwiched between facing sheet 20 and backing sheet 24 to distribute forces therebetween. As shown in FIGS. 2 and 3, free working end 30 and fixed end 32 are provided with adhesive coatings 40 and 42 on inner face 28 thereof. Fixed end 32 of first securing tape ribbon 27 is attached to backing sheet 24 on diaper outside surface 14 by means of adhesive coating 42 which can be made of a pressure-sensitive adhesive composition, a heat-activated or solvent-activated adhesive composition, or the like. Adhesive coating 40 is coextensive with free working end 30 but for distal end portion 97 and preferably is pressure-sensitive.

Tab 16 further includes second securing tape ribbon 47 having opposing inner and outer faces 48 and 49, grippable free working end 50 and fixed end 52. Outer face 49 of fixed end 52 of second securing tape ribbon 47 is substantially coextensive with, and adhesively but releasably attached to, the adhesive-coated first face 28 of free working end 30 of first securing tape ribbon 27. The adhesive bond between fixed end 52 and free working end 30 is at least as strong as the bond between fixed end 32 and outside surface 14 of backing sheet 24 so that ribbons 27 and 47 effectively perform as a single tab or ribbon during the initial diaper securement. Free working end 50 of second securing tape ribbon 47 extends beyond free working end 30 of first securing tape ribbon 27. A continuous adhesive coating 53 is provided along inner face 48 of substantially the entire second securing tape ribbon 47. Adhesive coating 53 is preferably a pressure-sensitive adhesive composition.

Release means 54 is provided and is adapted to be releasably attached to adhesive coating 53 on second securing tape ribbon 47. In the embodiment illustrated in FIGS. 2 and 3, release means 54 is carried by diaper 10 at a marginal location thereon to provide a release region facing in the same direction as diaper inside surface 12.

Second securing tape ribbon 47 is releasable from release means 54 to make pressure-sensitive adhesive coating 53 available for use in securing diaper 10 about an infant. Referring to FIGS. 2 and 3, first securing tape ribbon 27 and second securing tape ribbon 47 are folded about longitudinal edge 55 of diaper 10. Second securing tape ribbon 47 coacts with first securing tape ribbon 27 and provides securement means for initially fastening diaper 10 about an infant. The securement means can be moved from the folded-over, storage position of FIG. 2 in which adhesive coating 53 is releasably adhered to release means 54, to the extended, working position of FIG. 3 in which the adhesive coating 53 on inner face 48 of second securing tape ribbon 47 is available for use in securing diaper 10 about an infant. Adhesive coating 53 faces in the same direction as diaper inside surface 12 when second securing tape ribbon 47 is in the working position.

Thus, when tab 16 is in the extended working position of FIG. 3, free working end 30 of first securing tape ribbon 27 is adapted to secure diaper 10 about an infant by adhesive attachment to the outside surface 14 of the diaper via the second securing tape ribbon 47 which is carried entirely by free working end 30. Free working end 30 of first securing tape ribbon 27 is separable from fixed end 52 of second securing tape ribbon 47 to enable diaper 10 to be opened or removed from the infant, and to make adhesive coating 40 on free working end 30 of first securing tape ribbon 27 available for use in refastening diaper 10 about an infant. Free working end 30 of first securing tape ribbon 27 is thereby made detachable from and refastenable to second securing tape ribbon 47 for inspecting and/or repositioning the diaper about an infant. As illustrated in FIG. 3, free working end 30 is movable from the extended working position illustrated in solid lines wherein free working end 30 is adhesively attached to second securing tape ribbon 47, to the detached position illustrated in phantom wherein free working end 30 of first securing tape ribbon 27 is separated from second securing tape ribbon 47 which remains fastened to the diaper.

Diaper 10 can be fastened with tab 16 as depicted in FIG. 3. Fixed end 32 of first securing tape ribbon 27 is adhesively attached to one corner of diaper 10. When tab 16 is unfolded from the storage position of FIG. 2 to the working position of FIG. 3, tab 16 is adhesively fastened to an opposite corner of diaper 10 by means of adhesive coating 53 on second securing tape ribbon 47. The fastening of first securing tape ribbon 27 to diaper 10 via second securing tape ribbon 47 provides a good, strong closure means around the infant. When the diaper is in the fastened condition, fixed end 52 of second securing tape ribbon 47 lies between first securing tape ribbon 27 and diaper outside surface 14.

It is a feature of the present invention that when the diaper needs inspection or adjustment after an original closure has been made, the first securing tape ribbon 27 can be peeled from second securing tape ribbon 47 without disturbing the adhesive attachment of second securing tape ribbon 47 to diaper outside surface 14. This can be accomplished because the first securing tape ribbon 27 is adhesively but releasably attached to only a portion of second securing tape ribbon 47, i.e., the fixed end 52, so that stresses imposed on second securing tape ribbon 47 when first securing tape ribbon 27 is separated therefrom are imposed at a location spaced from the outermost edge 60 of second securing tape ribbon 47 which remains attached to the diaper. The free working end 50 extends beyond first securing tape ribbon 27, and preferably has a length at least as great as the width of second securing tape ribbon 47 to facilitate separation of second securing tape ribbon 47 from first securing tape ribbon 27.

First securing tape ribbon 27 can therefore be separated from second securing tape ribbon 47 and moved to the position illustrated in phantom in FIG. 3 to open a fastened diaper without resorting to tearing the outside surface of the diaper or the tab itself. When first securing tape ribbon 27 is separated from second securing tape ribbon 47, fixed end 32 of first securing tape ribbon 27 remains secured to one corner of diaper 10 while the second securing tape ribbon 47 remains fastened to the opposite corner of diaper 10 where the original closure was made. Second securing tape ribbon 47 acts as a reinforcing agent by remaining on the diaper where the original closure was made. The second securing tape ribbon adds strength to the area of the diaper which might otherwise tear upon peeling of first securing tape ribbon 27 from second securing tape ribbon 47 due to the stresses imposed on diaper 10 by the peeling action. When first and second tape ribbons 27 and 47 are separated from one another, diaper 10 can be inspected for soiling and/or can be readjusted for a better or neater fit around the infant.

When the inspection and/or adjustment is completed, diaper 10 is wrapped around the infant as was done originally and is refastened by positioning first securing tape ribbon 27 in an overlapping relationship with second securing tape ribbon 47 which remains attached to the opposite corner of diaper 10. Adhesive coating 40 on free working end 30 of first securing tape ribbon 27 is pressed against outer face 49 of second securing tape ribbon 47 to complete the closure. Since a portion of first and second tape ribbons 27 and 47, respectively, in overlapping relationship, or the attachment of ribbon 27 to diaper backing sheet 24, will furnish a sufficient adhesive closure, there need not be a complete overlapping alignment between the two tape ribbons upon subsequent refastenings. Thus, a looser fit around the infant can be attained by overlapping only a portion of free working end 30 of first securing tape ribbon 27 with second securing tape ribbon 47 or by securement without any overlap at all. Since second securing tape ribbon 47 is longer than free working end 30 of first securing tape ribbon 27, the fit of the diaper can be tightened by overlapping free working end 30 of first securing tape ribbon 27 with at least a portion of free working end 50 of second securing tape ribbon 47. Of course, when free working end 30 is adhesively attached directly to backing sheet 24, additional detachments and refastenings of the diaper will not be possible.

The refastened diaper is provided with a strong adhesive attachment because the adhesive material comprising adhesive coating 40 on free working end 30 remains thereon after the original closure is broken. The strength of the adhesive permits many openings and closures of the diaper.

As shown in FIGS. 2 and 3, release means 54 may comprise a ribbon segment or release strip having a release-coated surface on face 62 which provides the release region, and an adhesive coating on opposite face 64 by means of which the release strip is anchored to diaper inside surface 12. Alternatively, the release means may comprise a release layer which is a surface coating on a marginal position of the diaper inside surface 12, and preferably comprises a silicone release compound, or the like. The release strip or release layer preferably provides a release region of about the same width as tab 16 and is substantially coextensive with adhesive coating 53 on second securing tape ribbon 47. However, the release region may have a greater width than second securing tape ribbon 47 so as to provide for manufacturing tolerances.

While the distance between fixed end 52 of securing tape ribbon 47 and diaper longitudinal edge or margin 55 is not overly critical, this distance preferably should be sufficiently small so as to preclude substantial adhesion of a juxtaposed region of diaper backing sheet to an exposed adhesive region of pressure sensitive adhesive carried on face 28 when the diaper is releasably secured about an infant by means of securing tape ribbon 47. Undesirable adhesion can also be avoided by positioning tab 16 on diaper 10 so that the innermost edge of fixed end 52 abuts longitudinal edge 55.

The exposed adhesive region on inner face 28 can also be covered, if necessary or desirable, with a sheet or film material such as polyethylene, polyethylene terephthalate, cellulose, paper, or the like. In the alternative, an adhesive-free zone can be provided on the exposed region of face 28 between adhesive coatings 40 and 42.

Yet another possibility is to position release strip 54 so that the outermost end thereof extends beyond diaper edge 55 and a projecting portion of release strip 54 covers the exposed adhesive mass.

In the embodiment illustrated in FIG. 5, tab 116 is similar to tab 16 in FIGS. 2 and 3, but release means 154 comprises a separable cover strip 166 which is provided with a release coating on face 168 thereof and which is carried on second securing tape ribbon 147. The release coating is substantially coextensive with adhesive coating 153 and is removable therefrom. Cover strip 166 may be longer than second securing tape ribbon 147 and the inner end of cover strip 166 is preferably folded back about itself to provide gripping tab 169 which is easily grasped to facilitate removal of cover strip 166 from second securing tape ribbon 147.

Tab 216 in the embodiment illustrated in FIG. 6 is similar to tabs 16 and 116 in FIGS. 1–5 except for attached release strip 270. Release means 254 comprises cover strip 270 which is permanently attached to first securing tape ribbon 227. Cover strip 270 is provided with a release coating on face 272 thereof and is substantially coextensive with adhesive coating 253 and removable therefrom. Cover strip 270 is longer than second securing tape ribbon 247 and includes projecting portion 274 which extends beyond the innermost edge 276 of adhesive coating 253 and is adhesively attached to first securing tape ribbon 227. Cover strip 274 can be folded back about itself to adhesively attach projecting portion 274 to adhesive coating 240 on free working end 230 as depicted in FIG. 6, or can be interposed between first securing tape ribbon 227 and backing sheet 224 and adhesively attached to adhesive coating 242 on fixed end 232.

In the embodiment shown in FIG. 7, tab 316 is similar to tab 16 in FIGS. 2 and 3 and further includes a backing web 380 which is folded over about longitudinal edge 355 of the diaper to define first and second anchoring legs 382 and 384, respectively, each having an inner face 386 and an outer face 388. Anchoring legs 382 and 384 preferably are about equal in width and length, and are in a substantially juxtaposed relationship to one another, and receive a marginal portion of the diaper therebetween. An adhesive coating which may comprise a continuous adhesive coating 390 is provided on the inner face 386 of the anchoring legs. First anchoring leg 382 is permanently attached to facing sheet 320 on diaper inside surface 312 and second anchoring leg 384 is permanently attached to backing sheet 324 on diaper outside surface 314 by means of adhesive coating 390 which is substantially coextensive with both anchoring legs. Adhesive coating 390 can be a pressure-sensitive adhesive composition, a heat-activated or solvent-activated adhesive composition, or the like. Backing web 380 is attached to both the facing sheet 320 and backing sheet 324 to stiffen and strengthen the marginal portion of the diaper.

Fixed end 332 of first securing tape ribbon 327 is adhesively attached only to outer face 388 of second leg 384 by means of adhesive coating 342 which secures fixed end 332 to a marginal portion of the diaper. Release means 354 is provided on outer face 388 of first leg 382 and provides a release region facing in the same direction as diaper inside surface 312. Second securing tape ribbon 347 and free working end 330 of first securing tape ribbon 327 are movable from a folded-over storage position in which second securing tape ribbon 347 is releasably adhered to release means 354 to a working position in which the adhesive-coated second securing tape ribbon 347 is available for use in securing the diaper about an infant.

In all of the embodiments, it is desirable to provide a gripping means to facilitate separation of release means 54 and second securing tape ribbon 47 to expose adhesive coating 53 of second securing tape ribbon 47 preparatory to fastening the diaper about an infant. Free working end 50 is grippable and, as shown in FIGS. 2, 3 and 7, can also be provided with a projecting portion 92 which extends beyond outermost margin or edge 94 of adhesive coating 53, whereby outwardly extending portion 92 provides a gripping means for separating second securing tape ribbon 47 from release means 54 when fastening diaper 10 about an infant. Similarly, the permanently attached cover strip 270 in FIG. 6 can be provided with a projecting portion 295 which extends beyond outermost edge 296 of adhesive coating 253, whereby projecting portion 296 is a gripping means for separating cover strip 270 from adhesive-coated second securing tape ribbon 247. Furthermore, as described hereinabove, cover strip 166 in FIG. 5 includes gripping tab 169.

It is also desirable to provide a gripping means for separating first securing tape ribbon 27 from second securing tape ribbon 47 when removing the diaper from the infant. In all of the embodiments, distal end portion 97 of free working end 30 of first securing tape ribbon 27 projects beyond the outermost edge 98 of adhesive coating 40 on free working end 30. Projecting portion 97 provides a gripping means for separating the adhesive-coated free end 30 of first securing tape ribbon 27 from second securing tape ribbon 47. To facilitate separation of first and second tape ribbons 27 and 47, outer face 49 of second securing tape ribbon 47 preferably is slightly treated with a release compound to permit a relatively strong adhesive attachment between the tape ribbons while simultaneously enabling free working end 30 of first securing tape ribbon 27 to be separated from second securing tape ribbon 47. Alternatively, second securing tape ribbon 47 may be a material having the desired degree of inherent release properties.

If desired, adhesive coatings 40 and 42 on first securing tape ribbon 27 may be pressure-sensitive and together comprise a substantially continuous adhesive coating on inner face 28 of first securing tape ribbon 27.

Adhesive tabs suitable for the purposes of the present invention can be made from a wide variety of materials, provided that such materials are sufficiently flexible. Preferred materials for this purpose are polyalkylene webs such s polyethylene sheet, polypropylene sheet, and the like. Particularly preferred are webs which are oriented along the narrow dimension of the tab or webs which have filament reinforcements therein.

The pressure-sensitive layers such as adhesive coatings 40 and 53 are provided by applying a coating of a pressure-sensitive adhesive composition known in the art to be the appropriate surfaces of tape ribbons 27 and 47. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd$^2$ and densities of less than 0.15 g./cc., generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known to those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling second securing tape ribbon 47 and free working end 30 of first securing tape ribbon 27 away from the temporary engagement with release means 54, exposing adhesive coating 53 which was releasably adhered to release means 54. The tabs are then used to secure the diaper in the desired position by simply urging the pressure-sensitive adhesive surfaces in contact with the adjacent outer surface of the diaper, and can be detached and refastened as described hereinabove. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

a backing web, folded over to form first and second anchoring legs, each having an inner face and an outer face, and receiving a marginal portion of said diaper there-between, said inner face of said legs being provided with an adhesive coating by means of which said legs are permanently attached to said marginal portion, said first leg being attached to said diaper inside surface and said second leg being attached to said diaper outside surface;

a first securing tape ribbon having a fixed end and a free working end;

an adhesive coating on at least one face of said fixed end of said first securing tape ribbon by means of which said fixed end of said first securing tape ribbon is attached to said second leg to attach said fixed end to a marginal location of said diaper, and a pressure-sensitive adhesive coating on said one face of said free working end of said first securing tape ribbon;

a second securing tape ribbon having a fixed end and a grippable free working end, said fixed end of said second securing tape ribbon being coextensive with and adhesively but releasably attached to said adhesive-coated face of said free working end of said first securing tape ribbon and the free working end of said second securing tape ribbon extending beyond the free working end of said first securing tape ribbon, and a pressure-sensitive adhesive coating on said second securing ribbon on the face thereof opposite to the face attached to said free working end of said first securing tape ribbon; and release means on said outer face of said first leg providing a release region facing in the same direction as said diaper inside surface;

said second securing tape ribbon being movable from a folded-over storage position in which said second securing tape ribbon is releasably adhered to said release region to a working position in which said adhesive-coated second securing tape ribbon is available for use in securing said diaper about said infant; and said free working end of said first securing tape ribbon being separable from said fixed end of said second securing tape ribbon to enable said diaper to be removed from said infant and to make said pressure-sensitive adhesive coating on said free working end of said first securing tape ribbon available for use in refastening said diaper about said infant.

2. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

a backing web adhesively attached to the disposable diaper;

said backing web is folded over to form first and second substantially juxtaposed anchoring lgs, each having an inner face and an outer face, which anchoring legs receive a marginal portion of the diaper there-between;

a continuous, pressure-sensitive adhesive coating is provided on the inner faces of said anchoring legs and permanently attaches said anchoring legs to said marginal portion so that said first anchoring leg is attached to the diaper inside surface and said second anchoring leg is attached to the diaper outside surface;

a first securing tape ribbon having a fixed end and a free working end;

an adhesive coating on at least one face of said fixed end of said first securing tape ribbon by means of which said fixed end of said first securing tape ribbon is adhesively attached only to the outer face of said second anchoring leg, thereby securing the fixed end of said first securing tape ribbon to a marginal portion of the diaper, and a pressure-sensitive adhesive coating on said one face of said free working end of said first securing tape ribbon;

a second securing tape ribbon having a fixed end and a grippable free working end, said fixed end of said second securing tape ribbon being coextensive with and adhesively but releasably attached to said adhesive-coated face of said free working end of said first securing tape ribbon and the free working end of said second securing tape ribbon extending beyond the free working end of said first securing taper ribbon, and a pressure-sensitive adhesive coating on said second securing ribbon on the face thereof opposite to the face attached to said free working end of said first securing tape ribbon;

release means situated on the outer face of said first anchoring leg and facing in the same direction as the diaper inside surface;

said second securing taper ribbon is movable from a folded-over storage position, in which said second securing tape ribbon is releasably adhered to said release region, to a working position in which said adhesive-coated second securing tape ribbon is available for use in securing the diaper about the infant;

said free working end of said first securing tape ribbon being separable from said fixed end of said second securing tape ribbon to enable said diaper to be removed from said infant and to make said pressure-sensitive adhesive coating on said free working end of said first securing tape ribbon available for use in refastening said diaper about said infant; and a portion of each said free working end projects beyond the respective outermost edge of the pressure-sensitive adhesive coating on each said free working end and provides a gripping means.

* * * * *